US011191503B2

United States Patent
Moore et al.

(10) Patent No.: US 11,191,503 B2
(45) Date of Patent: Dec. 7, 2021

(54) FLUID-INJECTOR FOR A SIMULTANEOUS ANATOMICAL AND FLUID DYNAMIC ANALYSIS IN CORONARY ANGIOGRAPHY

(71) Applicant: International Business Machines Corporation, Armonk, NY (US)

(72) Inventors: Stephen Michael Moore, Melbourne (AU); Kerry J. Halupka, Northcote (AU); Yasmin Blunck, Brunswick West (AU); Sergiy Zhuk, Dublin (IR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 716 days.

(21) Appl. No.: 16/037,337

(22) Filed: Jul. 17, 2018

(65) Prior Publication Data

US 2020/0022664 A1   Jan. 23, 2020

(51) Int. Cl.
*A61B 6/00* (2006.01)
*A61M 5/00* (2006.01)
(Continued)

(52) U.S. Cl.
CPC .............. *A61B 6/504* (2013.01); *A61B 6/481* (2013.01); *A61M 5/007* (2013.01); *G16H 40/63* (2018.01);
(Continued)

(58) Field of Classification Search
CPC ....... A61B 6/504; A61B 6/481; A61B 6/5217; A61B 6/507; A61B 6/487; A61M 5/007;
(Continued)

(56) References Cited

U.S. PATENT DOCUMENTS

| 4,796,635 A | 1/1989 | Dumoulin |
| 5,419,325 A | 5/1995 | Dumoulin et al. |

(Continued)

FOREIGN PATENT DOCUMENTS

| CN | 101283910 A | 10/2008 |
| CN | 101756713 A | 6/2010 |

(Continued)

OTHER PUBLICATIONS

Scholtz et al. 2017 Cardiovasc. Diagn. Ther. 7:439-451 (Year: 2017).*

(Continued)

*Primary Examiner* — Michael J Tsai
*Assistant Examiner* — Patrick M Mehl
(74) *Attorney, Agent, or Firm* — Cantor Colburn LLP; Joseph Petrokaitis (57) ABSTRACT

A method for imaging a coronary arterial system of an individual includes releasing, using an actuator, pulses of a radio-opaque dye into a coronary arterial tree of the individual. The method further includes obtaining, using an image capture device, a sequence of invasive coronary x-ray angiogram images over time of the pulses of the radio-opaque dye. The method also includes tracking, using a processor, the pulses through the sequence of invasive coronary x-ray angiogram images and locating the pulses on a three dimensional (3D) structural model of the coronary arterial system to generate a three dimensional (3D) functional model of the coronary arterial system that shows a trajectory of the dye as it flows through different arterial branches.

16 Claims, 7 Drawing Sheets

(51) Int. Cl.
*G16H 40/63* (2018.01)
*G06T 7/00* (2017.01)

(52) U.S. Cl.
CPC .. *G06T 7/0012* (2013.01); *G06T 2207/30104* (2013.01)

(58) Field of Classification Search
CPC ...... A61M 2005/14208; A61M 5/1408; G16H 40/63; G16H 30/20; G16H 10/60; G16H 50/30; G06T 2207/30104; G06T 7/0012; G06T 2207/10016; G06T 2207/10116; G06T 7/0016
See application file for complete search history.

(56) References Cited

U.S. PATENT DOCUMENTS

| | | | |
|---|---|---|---|
| 5,485,831 | A | 1/1996 | Holdsworth et al. |
| 5,544,215 | A | 8/1996 | Shroy, Jr. et al. |
| 5,820,585 | A | 10/1998 | Mobin-Uddin et al. |
| 5,964,714 | A | 10/1999 | Lafontaine |
| 6,052,612 | A | 4/2000 | Desai |
| 6,343,514 | B1 | 2/2002 | Smith |
| 6,471,656 | B1 | 10/2002 | Shalman et al. |
| 9,396,535 | B2 | 7/2016 | Miyamoto |
| 9,943,277 | B2 | 4/2018 | Compas et al. |
| 2004/0254525 | A1* | 12/2004 | Uber, III ............... A61J 1/2096 604/67 |
| 2007/0078352 | A1 | 4/2007 | Pijls |
| 2009/0003521 | A1* | 1/2009 | Camus ................ A61B 6/5235 378/62 |
| 2013/0303920 | A1 | 11/2013 | Corl |
| 2014/0121513 | A1* | 5/2014 | Tolkowsky ........ A61B 5/02007 600/431 |
| 2015/0141853 | A1* | 5/2015 | Miller, III .......... A61B 5/02007 600/486 |
| 2015/0282777 | A1 | 10/2015 | Compas et al. |
| 2016/0196666 | A1 | 7/2016 | Venkatraghavan et al. |
| 2017/0325769 | A1* | 11/2017 | Venugopal ............. A61B 6/507 |

FOREIGN PATENT DOCUMENTS

| | | |
|---|---|---|
| WO | 9315658 A1 | 8/1993 |
| WO | WO9315658 A1 * | 8/1993 ............... A61B 6/00 |

OTHER PUBLICATIONS

International Search Report/Written Opinion; International Application No. PCT/IB2019/056010; International Filing Date: Jul. 15, 2019; dated Oct. 30, 2019; 8 pages.

Gibson, C.M., et al., 1996. "TIMI Frame Count", Circulation, 93(5), pp. 879-888.

Sibley, D.H., et al., "Subselective Measurement of Coronary Blood Flow Velocity Using a Steerable Doppler Catheter" Journal of the American College of Cardiology, 8(6), Dec. 1986, pp. 1332-1340.

* cited by examiner

FLUID-INJECTOR FOR A SIMULTANEOUS ANATOMICAL AND FLUID DYNAMIC ANALYSIS IN CORONARY ANGIOGRAPHY

BACKGROUND

The present invention generally relates in general to coronary angiography, and more specifically, to a fluid injector for a simultaneous anatomical and fluid dynamic analysis in coronary angiography.

Coronary angiography is a minimally invasive procedure for the diagnosis and treatment of cardiovascular disease. A conventional coronary angioplasty procedure includes guiding a catheter towards the coronary arteries, flushing with a radio-opaque dye, and dynamic imaging using an X-ray source. The procedure is usually repeated from different angles to provide a three-dimensional (3D) assessment of the vascular structure. A physician, such as a cardiologist, then visually interprets the images to assess for the presence, extent, and severity of the stenosis.

SUMMARY

Embodiments of the present invention are directed to a method for imaging a coronary arterial system of an individual. A non-limiting example of the method includes releasing, using an actuator, pulses of a radio-opaque dye into a coronary arterial tree of the individual. The method further includes obtaining, using an image capture device, a sequence of invasive coronary x-ray angiogram images over time of the pulses of the radio-opaque dye. The method also includes tracking, using a processor, the pulses through the sequence of invasive coronary x-ray angiogram images and locating the pulses on a three dimensional (3D) structural model of the coronary arterial system to generate a three dimensional (3D) functional model of the coronary arterial system that shows a trajectory of the dye as it flows through different arterial branches.

Embodiments of the present invention are also directed to a system for imaging a coronary arterial system of an individual. The system includes a catheter for insertion into a root of a coronary arterial tree. The catheter includes an inlet for receiving a radio-opaque and an outlet for releasing the radio-opaque dye into the coronary arterial tree. The system includes a pump coupled to the catheter. The pump is configured to pulse the radio-opaque dye into the coronary arterial tree. The system further includes a processor communicatively connected to the pump. The processor is operative to release pulses of the radio-opaque dye into the coronary arterial tree of the individual, obtain a sequence of angiogram images over time of the pulses of the radio-opaque dye, and track the pulses through the sequence of angiogram images and locate the pulses on a three dimensional (3D) structural model of the coronary arterial system to generate a 3D functional model of the coronary artery system that shows a trajectory of the dye as it flows through different arterial branches.

Embodiments of the present invention are directed to a computer program product. A non-limiting example of the computer program produce includes a computer readable storage medium having program instructions embodied therewith. The program instructions are executable by a processor to cause the processor to perform a method. The method includes releasing pulses of a radio-opaque dye into a coronary arterial tree of the individual. The method further includes obtaining a sequence of angiogram images over time of the pulses of the radio-opaque dye. The method includes tracking the pulses through the sequence of angiogram images and locating the pulses on a three dimensional (3D) structural model of the coronary arterial system to generate a three dimensional (3D) functional model of the coronary arterial system that shows a trajectory of the dye as it flows through different arterial branches.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Figure 1:
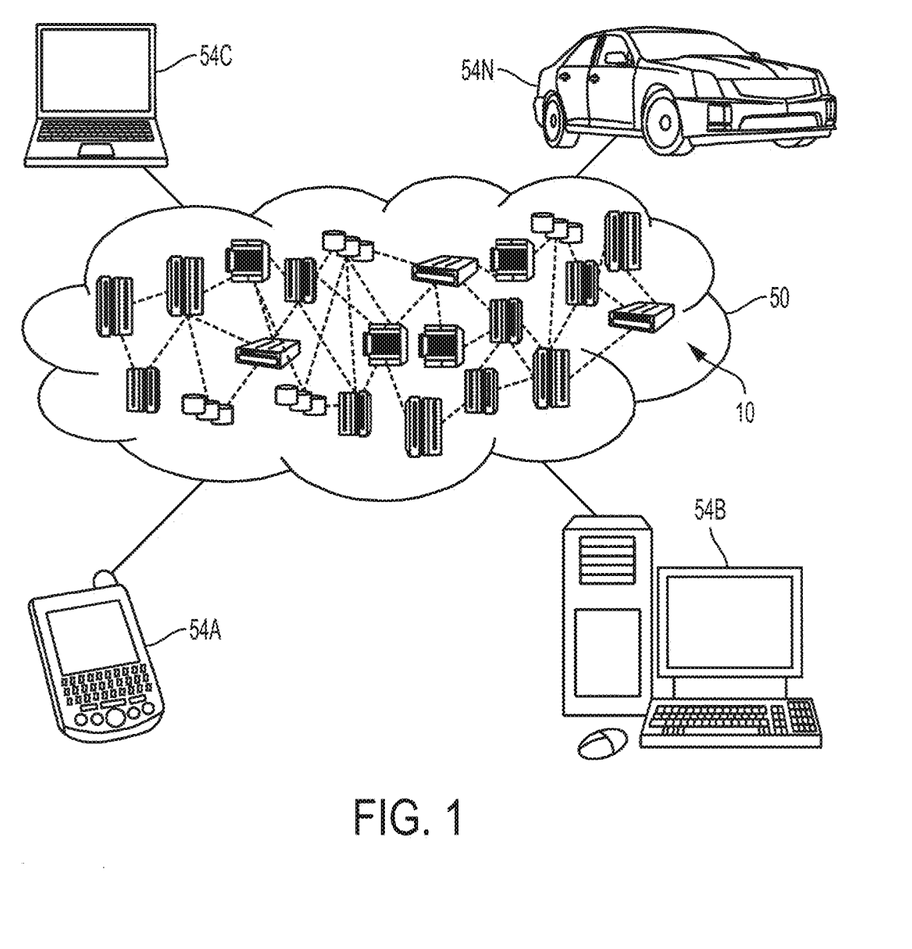
FIG. 1 depicts a cloud computing environment according to an embodiment of the present invention.

Referring now to FIG. 1, illustrative cloud computing environment 50 is depicted, according to an embodiment of the present invention. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
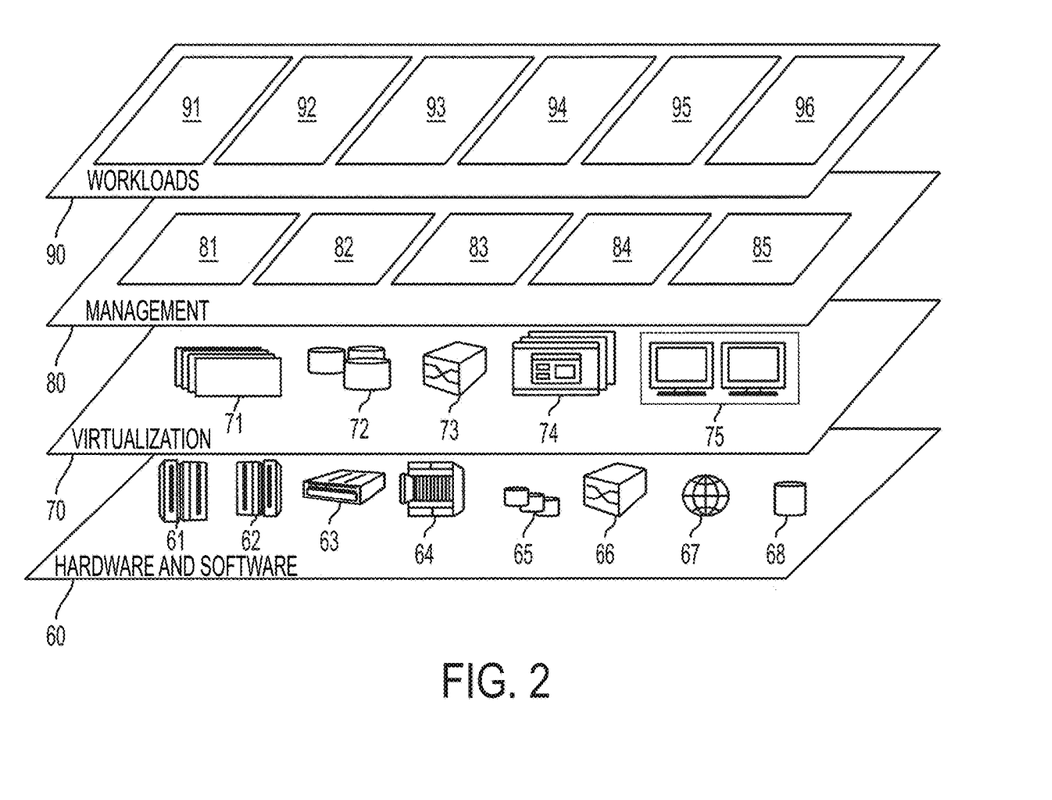
FIG. 2 depicts abstraction model layers according to an embodiment of the present invention.

Referring now to FIG. 2, a set of functional abstraction layers provided by cloud computing environment 50 (FIG. 1) is depicted, according to an embodiment of the present invention. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and imaging a coronary artery system of an individual 96.

Figure 3:
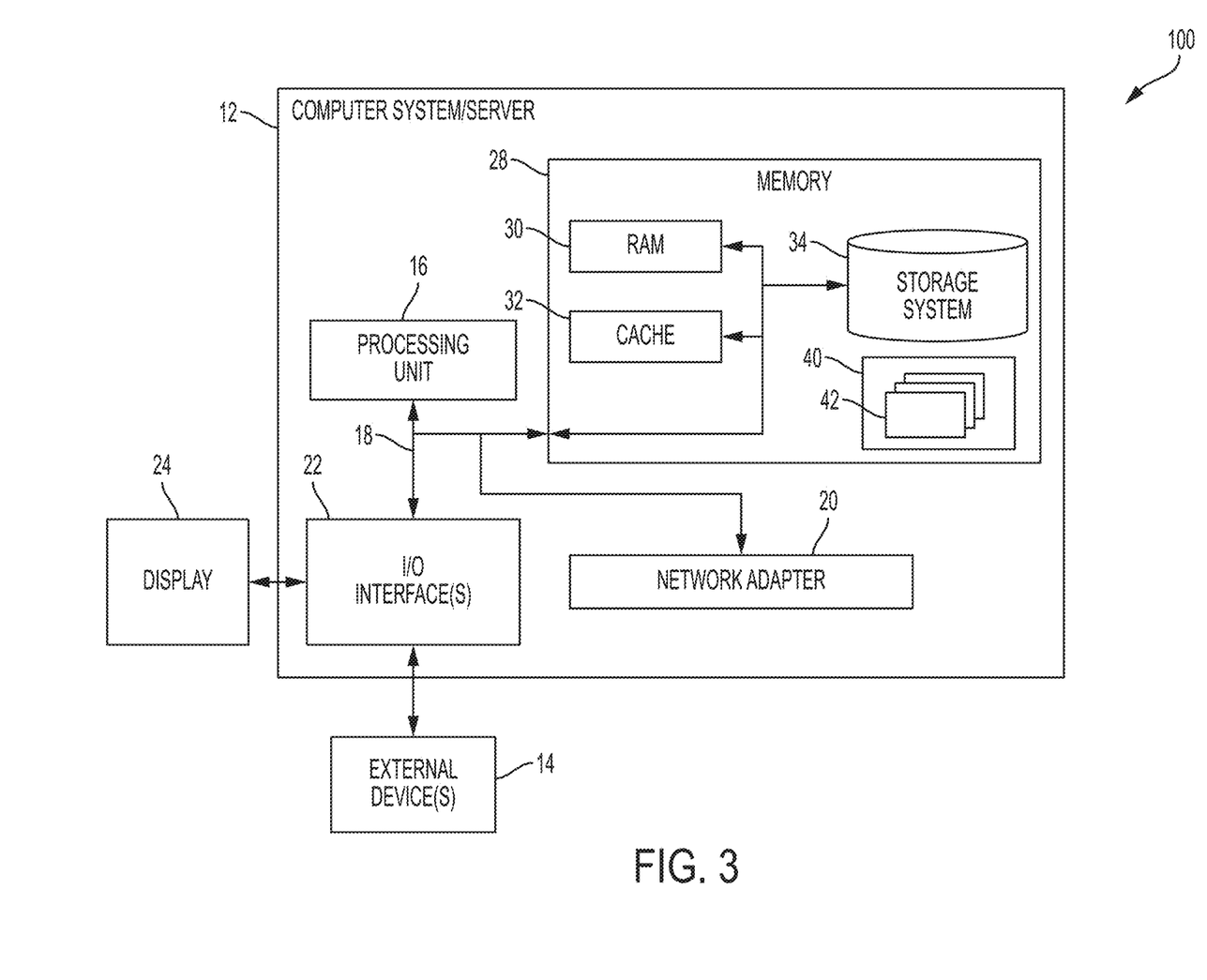
FIG. 3 depicts a computing node according to one or more embodiments of the present invention.

Referring now to FIG. 3, a schematic of a computing node 100 that can be included in a distributed cloud environment or cloud service network is shown according to a non-limiting embodiment of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100, according to one or more embodiments of the present invention, is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of technologies that are more specifically relevant to aspects of the invention, coronary angiograms provide valuable anatomical structural information. However, the angiograms include limited detail on actual cardiac function, which leaves the diagnosis and treatment plan a challenging process with potential for subjective and inaccurate decisions, and consequently inappropriate treatment actions. For example, patients with multiple narrowing of cardiac vessels are in particular risk of mistreatment, as the differentiation between harmful, flow-limiting stenoses and innocuous narrowings is often challenging and unreliable.

Assessment tools and functional measurements have been developed for use alongside coronary angiograms. For example, the coronary flow reserve (CFR), which is the ratio of maximal hyperemic to basal coronary flow velocity, and the myocardial fractional flow reserve (FFR), which is the ratio of distal coronary pressure to aortic pressure, are widely recognized as additional diagnostic indices for interpreting the physiological impact of individual stenosis. Such measures are, however, not routinely applied in clinical practice, as conventional approaches include invasive (Doppler guide-wires), semi-invasive (transesophageal probe), and/or expensive (positron emission tomography) procedures.

Recent clinical trials strongly support incorporating physiological measurements, such as FFR, for improved diagnosis and treatment planning. Standard FFR acquisitions involve a specialized catheter that is equipped with a pressure transducer to record blood pressure upstream and downstream of the vessel narrowing. The ratio of pressure readings around the stenoses are indicative of hemodynamic significance of the bespoke narrowing. Although shown to improve patient outcomes, the additional cost, time, training requirements, and potential difficulties during the FFR procedure have resulted in a relatively low uptake of the technique into clinical practice.

Turning now to an overview of the aspects of the invention, one or more embodiments of the invention address the above-described shortcomings of the prior art by providing methods and systems that include a pulsed injector (including a catheter and pump) as part of a coronary fluoroscopy fluid-injection system. The pump is coupled to the catheter and configured to pulse the radio-opaque dye into the coronary artery. The pulsed injector releases pulses of the radio-opaque dye into the coronary artery system. The dye front is tracked over time as it moves with the blood flow through the coronary artery system, and the arrival times of the dye front over time are mapped onto a 3D coronary tree. The methods and systems according to embodiment of the invention enable the simultaneous assessment of coronary structure and stenosis detection, as well as functional assessment of FFR for the interpretation of the impact and severity of any detected stenosis. The methods and systems according to embodiments of the invention thus provide the capability of performing real-time assessment of fluid dynamics.

The above-described aspects of the invention address the shortcomings of the prior art by using an injector system that pulses a radio-opaque fluid that can be tracked to a 3D model of arterial structure to determine arrival times of the radio-opaque fluid within the structure. Embodiments of the invention provide simultaneous information on both anatomical coronary structure and functional fluid dynamics, which provides physicians with information that enables differentiation between harmful flow-limiting stenosis and innocuous narrowings.

Figure 4:
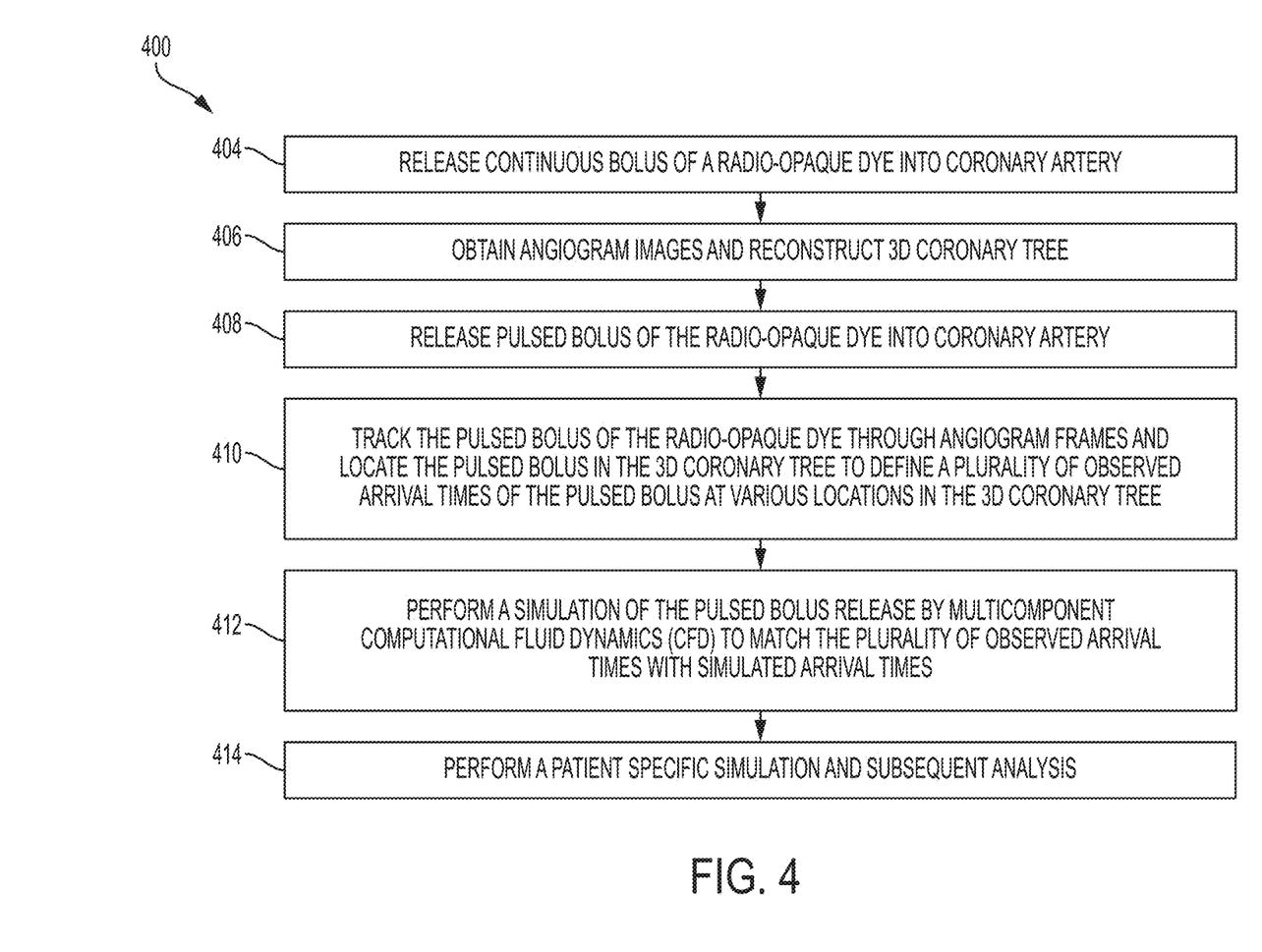
FIG. 4 depicts a flow diagram illustrating a method for imaging a coronary artery system according to one or more embodiments of the present invention.

Turning now to a more detailed description of aspects of the present invention, FIG. 4 depicts a flow diagram illustrating a method 400 for imaging a coronary artery system according to one or more embodiments of the present invention. Initially, a catheter is inserted into a coronary artery. The catheter is a hollow tube, with an inlet and an outlet. The inlet receives the dye, and the outlet releases the dye into the coronary artery. The catheter is inserted through the groin or wrist of an individual, such as a human patient, and then navigated to the root of the coronary artery.

The method 400 includes, as shown in box 404, releasing a continuous bolus of a radio-opaque dye (also referred to as contrast) into the coronary artery. The continuous bolus of radio-opaque dye is continuously injected through the catheter using a syringe, such as a motorized syringe, and a pump. The radio-opaque dye fills the coronary artery and its branches with dye to provide sufficient contrast between the artery and the surrounding tissue for visualization on an X-ray. The radio-opaque dye acts as a contrast agent that is carried with the blood flow into smaller branches of the arterial tree and ultimately into the tissues and veins.

The method 400 includes, as shown in box 406, obtaining angiograms images (also referred to as X-ray images) and reconstructing a 3D coronary tree. The angiogram images are taken after the radio-opaque dye has moved through the arterial tree. A limited number of angiogram images are taken, for example, between one and ten images. According to one or more embodiments of the invention, angiogram images are taken from at least two different views or angles. To obtain the different views, the individual can be moved between the frames so that each image is of a different region. Using the angiogram images taken from different views, a 3D reconstruction of the coronary tree geometry is formed from the segmented and back projected arterial structures provided by the angiogram images. The 3D reconstructions provides structural anatomical information through observation of the arterial structure.

The method 400 includes, as shown in box 408, releasing a pulsed bolus of the radio-opaque dye into the coronary artery. An electrocardiogram (ECG) trace is taken prior to injecting the pulsed bolus. The ECG records the electrical activity of the heart during the cardiac cycle. The ECG trace is used to gate the release of the pulsed bolus of radio-opaque dye, such that the pulse can be released at multiple different time points within the cardiac cycle (e.g. during systole, diastole, in-between).

The pulsed bolus of the radio-opaque dye is released from at least one view or angle. To obtain different views, the patient can be moved between the frames so that each image is of a different region.

According to one or more embodiments of the present invention, the pulsed bolus of the radio-opaque dye is released by multiple pulses, for example, 2 to 10 pulses, by a motorized pump. According to some embodiments of the present invention, the pulsed bolus of the radio-opaque dye is released by 2, 3, 4, 5, 6, 7, 8, 9, or 10 pulses. According to other embodiments of the invention, the radio-opaque dye is pulsed by alternate injection with a non-radio-opaque dye. Alternating injections of a radio-opaque dye with a non-radio-opaque dye creates observed pulses of the radio-opaque dye. The catheter for the alternative injections can include two separate hollow ports or fluid chambers, one for each dye, according to some embodiments of the present invention. The fluid injector can include two or more fluid chamber according to some embodiments of the present invention.

The method 400 includes, as shown in box 410, tracking the pulsed bolus of the radio-opaque dye through angiogram frames and locating the pulsed bolus in the 3D coronary tree to define a plurality of observed arrival times of the pulsed bolus at various locations in the 3D coronary tree. A sequence of angiogram frames are collected over time. According to one or more embodiments of the present invention, about 50 to about 100 frames are collected, at a frequency of about 10 to about 30 frames per second. The dye front moves with the blood flow through the arteries and will have different arrival times at different positions within the arterial tree. The position of the dye front at various times (plurality of observed arrival times) are then located on the 3D coronary tree model (see also FIG. 6) to show a trajectory of the dye front as it flows along the different arterial branches, which provides functional information describing the blood flow.

With a standard injection protocol, the dye front is only visible in the first few subset of angiogram frames; once the dye has reached the end of the major arteries, all of the vascular anatomy of interest is visible, but the dye motion is no longer visible. However, by using an injection system as described herein that can create and release pulses of radio-opaque dye, the dye front can be continually tracked to provide much more functional information as the coronary arteries exhibit a large range of motion over time (between angiogram frames) due to the beating of the heart. For example, between subsequent angiogram frames, a pulse of dye will exhibit both a significant axial motion along an artery and a significant translational motion as the artery moves with the heart, which will be captured in the 3D functional model.

The method 400 includes, as shown in box 412, performing a simulation of the pulsed bolus release by multicomponent computational fluid dynamics (CFD) to match the plurality of observed arrival times with simulated arrival times. Any advanced biophysical modeling procedure can be used to perform the simulation.

According to one or more embodiments of the invention, a real-time cloud based virtual fractional flow reserve (FFR) estimation can be used. The real-time cloud based system for estimating FFR can include a front end application to receive image frames from an imaging system (angiogram frames) to develop a model of the coronary artery system based on an observed arrival times of the dye front at locations within the model. A graphics processing unit is configured to represent computed arrival times in the coronary artery system using a Lattice-Boltzmann Method (LBM) to generate a representation of the coronary artery system. A dynamic controller tunes a velocity field based on a mismatch between the observed arrival times and the computed arrival times at the locations within the model to obtain a best estimate of the velocity field to perform a FFR measurement.

The method 400 includes, as shown in box 414, performing a patient specific simulation of the pulsed bolus release and subsequent analysis. The patient specific simulation includes computing a numerical solution to the 3D unsteady transport equations describing the motion of the blood and contrast agent. The underlying equations can include either the incompressible Navier-Stokes equations to describe the blood or a passive scalar transport equation to describe the contrast agent, or a set of multicomponent conservation equations for the blood and contrast agent respectively. The simulation requires as input a specification of the patient's systemic blood pressure waveform (obtained during cardiac catheterization as a standard practice) and the contrast release profile (i.e., the flowrate and timing of the release—which would be programmed into the motorized pump) to be applied as inlet boundary conditions to the patient specific computational model. At the outlets of the coronary tree, zero-D (0-D) lumped parameter electrical network style models (which include resistances and capacitances) are applied to represent the downstream vasculature that is not included in the computational model. The optimization process begins by initializing the outlet resistances to random values (but within a reasonable range that would for un-physiologically low or high flowrates) and performing a 'forward solution', simulating the motion of the blood and contrast agent through the coronary tree models and recording the arrival time of the contrast agent at the points that were tracked from the angiograms. The mismatch between the 'observed' and 'simulated' arrival times of the contrast at these points is used to define a 'misfit' which can be used to adjust the outlet resistances. A complete simulation hence includes multiple forward solutions, iteratively simulating the contrast motion and adjusting the peripheral resistances until the mismatch observed and simulated arrival time is minimized to some user specified tolerance. At this point is can be inferred that the set of peripheral outlet resistances accurately models the individual patients coronary tree, and the pressure loss through a stenosis can be measured (possibly by performing one final simulation without the contrast motion such that the pressure loss is defined solely in terms of the blood flow through the stenosis).

The method 400 further includes (not shown) assessing, based on the patient specific simulation, a hemodynamic significance of stenosis to determine patient diagnosis and treatment. The patient specific simulation provides a model of both anatomical and functional information, which allows a physician to more accurately determine an appropriate course of treatment. The combined anatomical and functional information assists physicians with treating patients with complex problems, such as multiple narrowing of cardiac vessels, as such patients are in particular risk of mistreatment due to the difficulties in differentiating between harmful flow limiting stenosis and innocuous narrowings.

Figure 5:
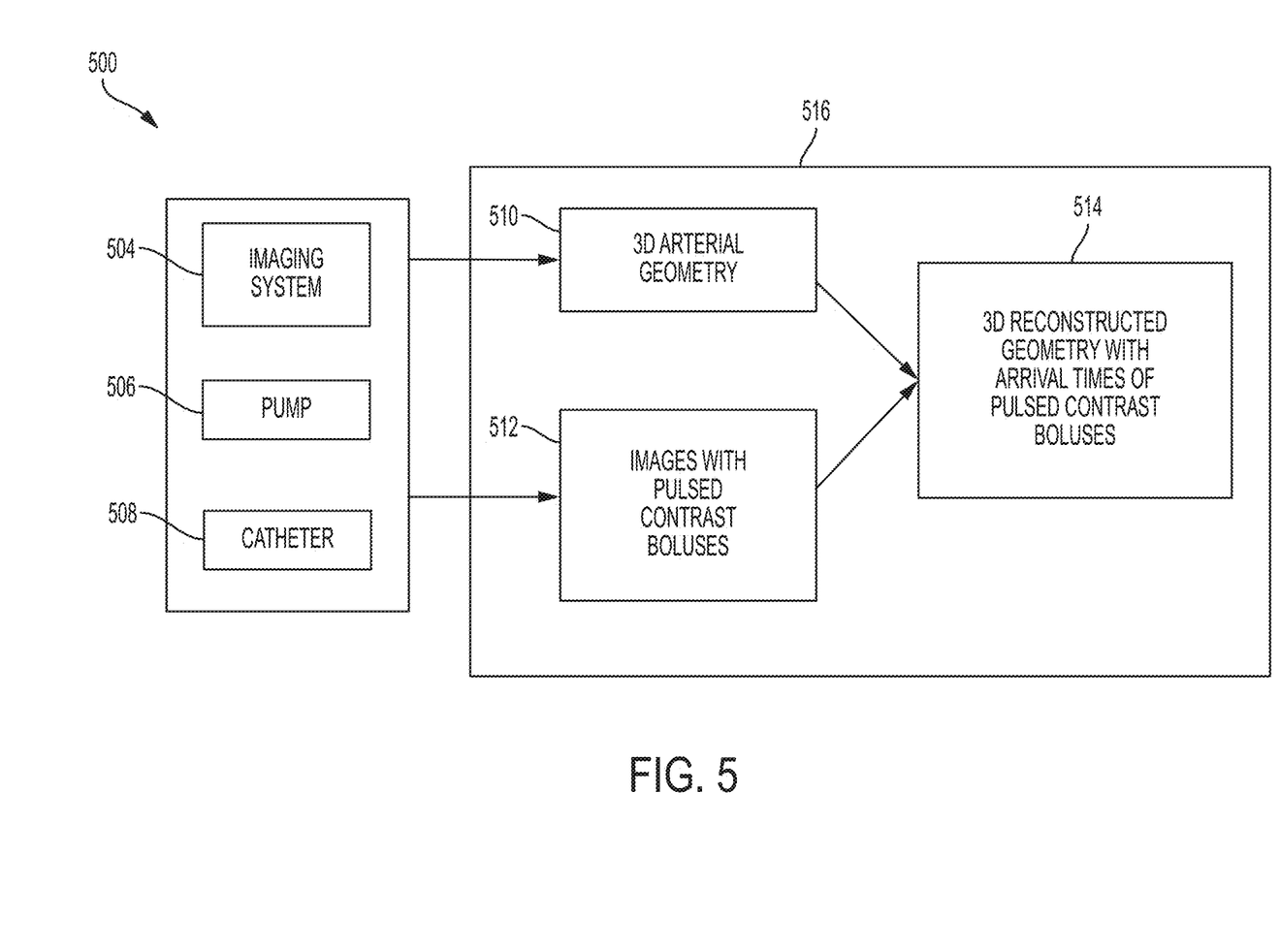
FIG. 5 depicts a diagram illustrating a system for imaging a coronary artery system according to one or more embodiments of the present invention.

FIG. 5 depicts a diagram illustrating an exemplary system 500 for imaging a coronary artery system according to one or more embodiments of the present invention. The system 500 includes an imaging system 504, such as an X-ray machine. The imaging system 504 collects images, such as angiographic images, of a patient's coronary artery system.

The system 500 includes at least one pump 506 and a catheter 508. The catheter 508 is inserted and guided into a coronary artery of a patient. The catheter 508 is inserted through the groin or wrist and then navigated to the root of the coronary artery. The pump 506 releases multiple pulses of a radio-opaque dye. The pump 506 can release multiple pulses through a single hollow port catheter 508 according to some embodiments of the invention. According to other embodiments of the invention, the radio-opaque dye is pulsed by alternate injection with a non-radio-opaque dye. Alternating injections of a radio-opaque dye with a non-radio-opaque dye creates observed pulses of the radio-opaque dye. The catheter 508 in such embodiments can include two separate hollow ports, one for each dye. A fluid injector also can include two or more fluid chambers according to some embodiments of the present invention. The pump 506 also can be capable of injecting a continuous bolus of radio-opaque dye. Alternatively, a second pump can be included that is capable of injecting a continuous bolus of radio-opaque dye.

A continuous bolus of radio-opaque dye is injected and allowed to flow through the coronary artery system. The imaging system 504 tracks the flow of the radio-opaque dye. The system 500 includes a processor 516 that collects two or more angiogram views and reconstructs a 3D arterial geometry 510 tree from the segmented and back projected arterial structure. The 3D arterial geometry tree 510 is a model of the coronary artery system of the patient that includes a model of arterial centerlines (skeleton) that is visualized as a set of line segments defined by a set of coordinates in 3D space. Software creates the skeletons from angiographic images. Angiogram images with the pulsed contrast boluses 512 are also collected over time. The pulsed dye is tracked through the angiogram frames, and the dye front is located in the 3D arterial geometry 510 tree to provide a 3D reconstructed geometry with arrival times of the pulsed contrast boluses 514.

Figure 6:
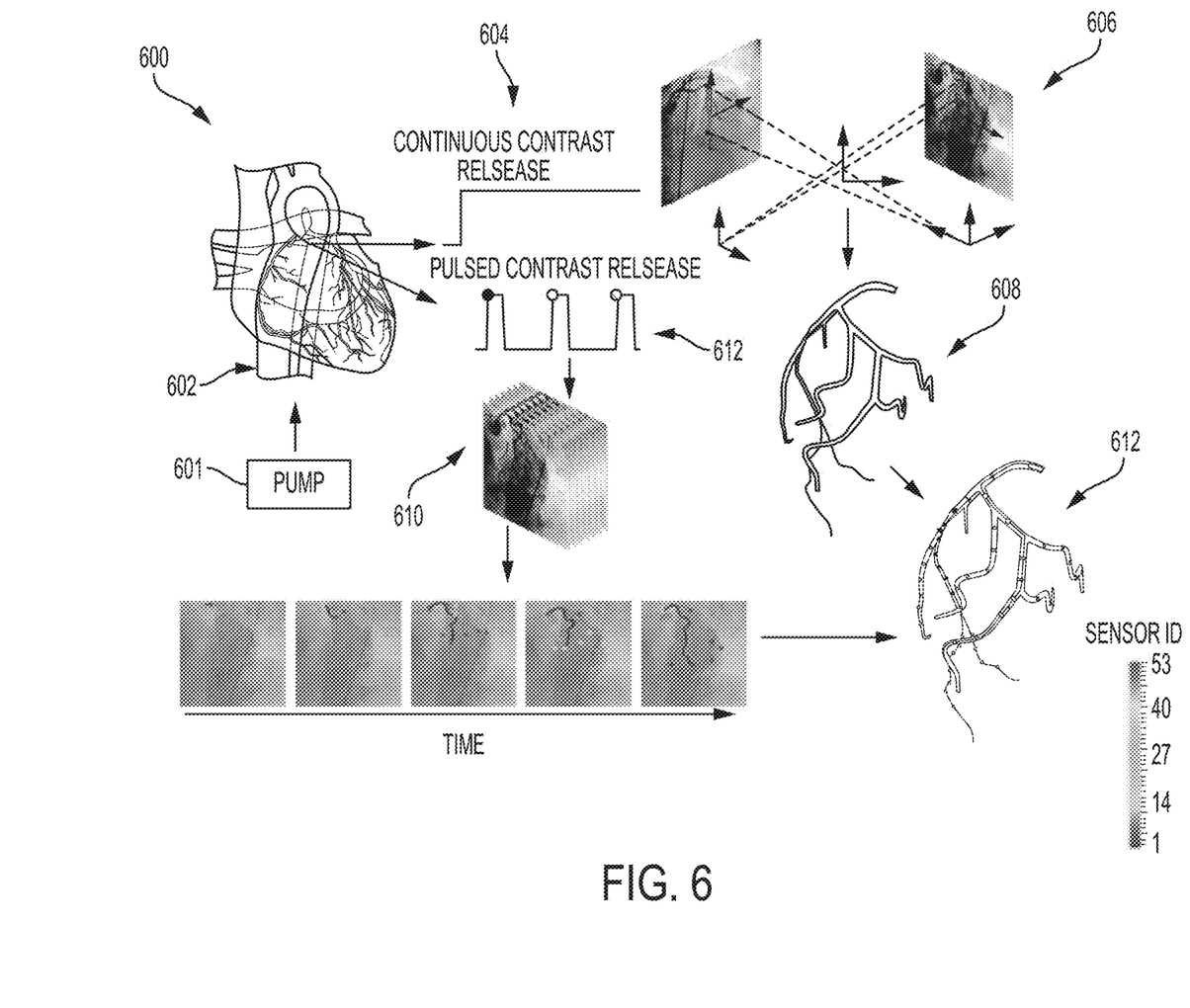
FIG. 6 depicts a diagram illustrating an exemplary method for imaging a coronary artery system according to one or more embodiments of the present invention.

FIG. 6 depicts a diagram illustrating an exemplary system 600 for imaging a coronary artery system according to one or more embodiments of the present invention. A catheter is inserted through the groin or wrist of a patient and navigated to the root of the coronary artery 602. A pump 601 releases a continuous bolus 604 of contrast (radio-opaque dye) through the catheter, which is flowed through the coronary artery system of a patient. Angiogram images 606 from two or more views are used to reconstruct a 3D coronary geometry tree 608. The pump 601, which can be the same or different than the pump used to release the continuous bolus 604, pulses boluses of contrast 612 through the coronary artery system. A plurality of angiogram images 610 displaying the pulsed boluses are collected over time. The dye front is tracked through the plurality of angiogram images 610 and located in the 3D coronary geometry tree 608 to form a 3D image 612 that provides both structural and functional information about the patient's coronary blood flow over time.

Figure 7A:
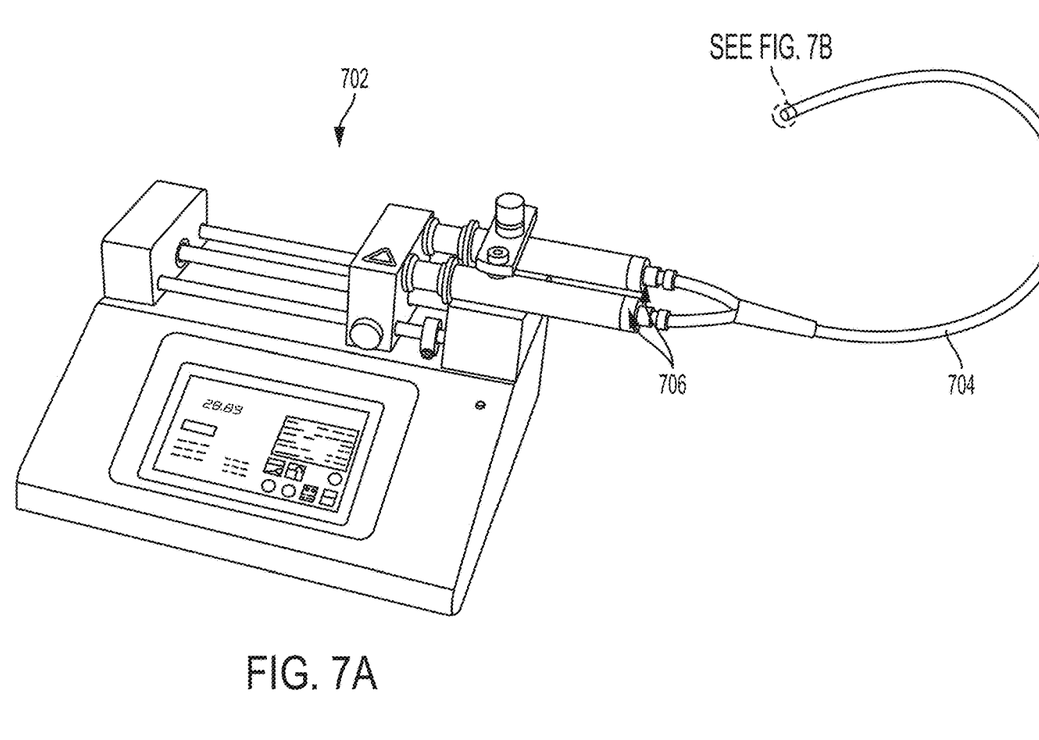
FIG. 7A depicts a diagram illustrating an exemplary catheter and pump for imaging a coronary artery system according to one or more embodiments of the present invention.
Figure 7B:
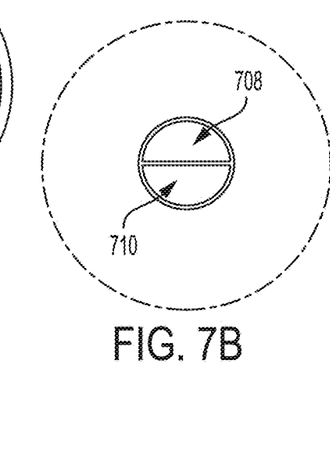
FIG. 7B depicts an expanded cross-sectional view of the catheter shown in FIG. 7A according to one or more embodiments of the present invention.

FIG. 7A depicts a diagram illustrating an exemplary catheter 706 and pump 702 for imaging a coronary artery system according to one or more embodiments of the present invention. FIG. 7B depicts an expanded cross-sectional view of the catheter 706 shown in FIG. 7A according to one or more embodiments of the present invention. The pump 702 is programmable and capable of being programmed to inject quick and small alternating boluses of two fluids, such as contrast and non-contrast dyes, e.g., saline. The bolus can be released with flowrates ranging, for example, from 1-100 mL/min over time periods ranging, for example, from 0.1-0.5 s. The pump 702 includes two syringes 704, which are coupled to the catheter 706. The catheter 706 is split, as shown in the cross-sectional view of FIG. 7B, to include two separate fluid chambers 708, 710.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method for imaging a coronary arterial system of an individual, the method comprising:
   releasing a continuous bolus of a radio-opaque dye into the coronary arterial system;
   obtaining a plurality of first angiogram images from two or more views of the individual;
   reconstructing, from the first angiogram images, a three dimensional (3D) structural model comprising a coronary tree geometry of the coronary arterial system of the individual;
   administering an electrocardiogram (ECG) trace;
   releasing, using an actuator, a pulsed bolus of a radio-opaque dye into the coronary arterial system of the individual, wherein the ECG trace is used to gate the release of the pulsed bolus;

obtaining, using an image capture device comprising one of an X-ray imaging system and a CT system, a sequence of second angiogram images over time;

tracking, using a processor, pulses of the pulsed bolus through the sequence of second angiogram images and locating the pulses on the 3D structural model to generate a 3D functional model of the coronary arterial system that shows a trajectory of the radio-opaque dye as it flows through different arterial branches; and performing a simulation specific to the individual that shows the pulses of the radio-opaque dye flowing through the individual's coronary arterial system, wherein performing the simulation includes computing a numerical solution to 3D unsteady transport equations describing the motion of the individual's blood and the radio-opaque dye.

2. The method of claim 1 further comprising, prior to releasing the pulses, inserting a catheter into a root of the coronary artery.

3. The method of claim 2, wherein the catheter includes two separate fluid chambers.

4. The method of claim 1, wherein a non-radio-opaque dye alternates with the pulses of the radio-opaque dye.

5. The method of claim 1 further comprising subsequent to tracking and locating the pulses, performing a simulation of the pulses of the radio-opaque dye moving through the coronary artery system to match a plurality of observed arrival times at various locations in the coronary artery system with simulated arrival times.

6. The method of claim 5, wherein the simulation comprises multicomponent computational fluid dynamics (CFD).

7. A system for imaging a coronary artery system of an individual, the system comprising:
a catheter for insertion into a root of a coronary arterial tree, the catheter having an inlet for receiving a radio-opaque dye and an outlet for releasing the radio-opaque dye into the coronary arterial tree;
a pump coupled to the catheter, the pump configured to pulse the radio-opaque dye into the coronary arterial tree; and
a processor communicatively connected to the pump, the processor operative to:
release a continuous bolus of a radio-opaque dye into the coronary arterial tree;
obtain a plurality of first angiogram images from two or more views of the individual;
reconstruct, from the first angiogram images, a three dimensional (3D) structural model comprising a coronary tree geometry of the coronary arterial system of the individual;
administer an electrocardiogram (ECG) trace;
release a pulsed bolus of the radio-opaque dye into the coronary arterial tree of the individual, wherein the ECG trace is used to gate the release of the pulsed bolus;
obtain a sequence of second angiogram images over time;
track pulses of the pulsed bolus through the sequence of second angiogram images and locate the pulses on the 3D structural model to generate a 3D functional model of the coronary arterial system that shows a trajectory of the radio-opaque dye as it flows through different arterial branches; and
perform a simulation specific to the individual that shows the pulses of the radio-opaque dye flowing through the individual's coronary arterial system, wherein performing the simulation includes computing a numerical solution to 3D unsteady transport equations describing the motion of the individual's blood and the radio-opaque dye.

8. The system of claim 7, wherein the catheter includes two separate fluid chambers.

9. The system of claim 7, wherein a non-radio-opaque dye alternates with the pulses of the radio-opaque dye.

10. The system of claim 7, wherein the processor is further operative to, subsequent to track and locate the pulses, perform a simulation of the pulses of the radio-opaque dye moving through the coronary arterial system to match a plurality of observed arrival times at various locations in the coronary arterial system with simulated arrival times.

11. The system of claim 10, wherein the simulation comprises multicomponent computational fluid dynamics (CFD).

12. A computer program product comprising a processor, memory, and non-transitory computer readable storage medium having program instructions embodied therewith, the program instructions executable by the processor to cause the processor to perform a method comprising:
releasing a continuous bolus of a radio-opaque dye into a coronary arterial system of an individual;
obtaining a plurality of first angiogram images from two or more views of the individual;
reconstructing, from the first angiogram images, a three dimensional (3D) structural model comprising a coronary tree geometry of the coronary arterial system of the individual;
administering an electrocardiogram (ECG) trace;
releasing a pulsed bolus of a radio-opaque dye into the coronary arterial system tree of the individual, wherein the ECG trace is used to gate the release of the pulsed bolus;
obtaining a sequence of second angiogram images over time;
tracking the pulses of the pulsed bolus through the sequence of second angiogram images and locating the pulses on the 3D structural model to generate a 3D functional model of the coronary arterial system that shows a trajectory of the radio-opaque dye as it flows through different arterial branches; and
performing a simulation specific to the individual that shows the pulses of the radio-opaque dye flowing through the individual's coronary arterial system, wherein performing the simulation includes computing a numerical solution to 3D unsteady transport equations describing the motion of the individual's blood and the radio-opaque dye.

13. The computer program product of claim 12, wherein the pulses are released into a catheter arranged at the root of the coronary arterial tree and the catheter includes two separate fluid chambers.

14. The computer program product of claim 12, wherein a non-radio-opaque dye alternates with the pulses of the radio-opaque dye.

15. The computer program product of claim 12, the method further comprising, subsequent to tracking and locating the pulses, performing a simulation of the pulses of the radio-opaque dye moving through the coronary arterial system to match a plurality of observed arrival times at various locations in the coronary arterial system with simulated arrival times.

16. The computer program product of claim 12, wherein the simulation comprises multicomponent computational fluid dynamics (CFD).

* * * * *